(12) United States Patent
Buford

(10) Patent No.: US 11,014,025 B1
(45) Date of Patent: *May 25, 2021

(54) PRESSURIZED FILTRATION SYSTEM AND DEVICE FOR RAPID EXTRACTION AND RECYCLING OF MEDICATION FROM BODY FLUID

(71) Applicant: Kevin-Steven Creagh Buford, New Orleans, LA (US)

(72) Inventor: Kevin-Steven Creagh Buford, New Orleans, LA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/830,056

(22) Filed: Mar. 25, 2020

Related U.S. Application Data

(60) Provisional application No. 62/986,060, filed on Mar. 6, 2020.

(51) Int. Cl.
*B01D 29/56* (2006.01)

(52) U.S. Cl.
CPC ........ *B01D 29/56* (2013.01); *B01D 2201/202* (2013.01); *B01D 2221/10* (2013.01)

(58) Field of Classification Search
CPC .......... A61F 5/451; A61J 3/02; B01D 61/022; B01D 61/18; B01D 63/082; B01D 2257/70; B01D 2257/91; B01D 2315/16
See application file for complete search history.

(56) References Cited

U.S. PATENT DOCUMENTS

| | | |
|---|---|---|
| 5,076,933 A | 12/1991 | Glenn et al. |
| 2002/0035750 A1 | 3/2002 | Braxton |
| 2006/0011545 A1 | 1/2006 | Latza |
| 2013/0102948 A1 | 4/2013 | Reich et al. |
| 2014/0042094 A1 | 2/2014 | Montagu |
| 2014/0231331 A1 | 8/2014 | de los Reyes et al. |
| 2015/0050706 A1 | 2/2015 | Buekenhoudt et al. |
| 2015/0209731 A1 | 7/2015 | Vander Hoff et al. |

FOREIGN PATENT DOCUMENTS

DE 4129041 A1 * 3/1993 ............... C07K 1/36

OTHER PUBLICATIONS

International Search Report for Application No. PCT/2020/26006 dated Jun. 29, 2020.
Written Opinion of International Patent Application No. PCT/2020/26006.
International Search Report for Application No. PCT/US/20/26006 dated Jun. 29, 2020.

* cited by examiner

*Primary Examiner* — Dirk R Bass
(74) *Attorney, Agent, or Firm* — McBee Moore & Vanik IP, LLC

(57) ABSTRACT

The present disclosure relates to a system for the selective extraction and recycling of medication from body fluid, using a pressurized filtration system and device. The disclosure further relates to methods for extracting and/or recycling medication from body fluid in a pressurized system and methods of using the medication collected/extracted from that body fluid.

19 Claims, 4 Drawing Sheets

Figure 1:
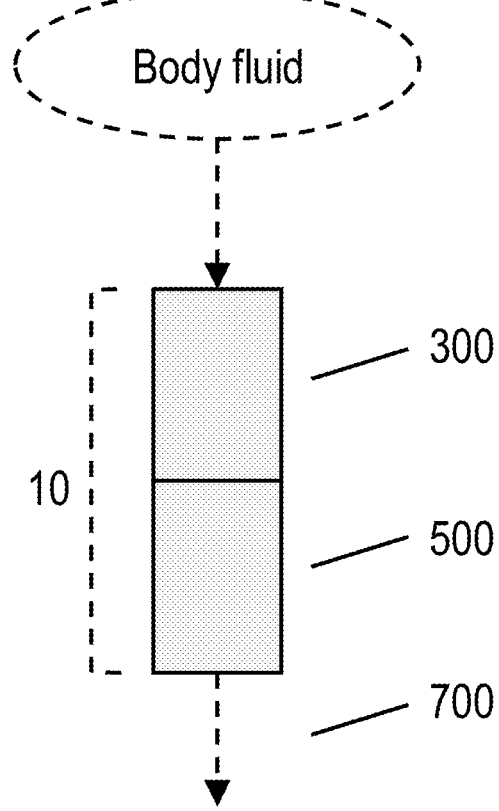

PRESSURIZED FILTRATION SYSTEM AND DEVICE FOR RAPID EXTRACTION AND RECYCLING OF MEDICATION FROM BODY FLUID

CROSS-REFERENCE TO RELATED APPLICATIONS

This application claims the benefit of U.S. Provisional Application No. 62/986,060, filed Mar. 6, 2020, the contents of which are herein incorporated by reference in their entirety.

FIELD OF INVENTION

The present disclosure relates to a method and device for the selective extraction and recycling of medication, including but not limited to naturally occurring or engineered hormones, chemicals, antibodies, enzymes, lipids, proteins or pharmaceutical products from already liquified or liquefiable body matter; non-limiting examples include tears, sweat, saliva, urine, blood, feces/tissue, which will be collectively referred to as "body fluid", all using a Pressurized Filtration System.

BACKGROUND OF THE INVENTION

In large scale bioterrorism, epidemics, and world-wide pandemics, medications will run out and there will be insufficient quantity to treat exposed, sick, poisoned, exposed or infected people. Recycling and recovering medication and their metabolites from body fluid dramatically increases the overall amount of medication available to treat the population, and number of lives saved.

During the recent H1N1 (swine flu) virus epidemic, countries with antiviral factories began to hoard antiviral medication as well as their necessary critical ingredients and reagents and their exportation to other countries was stopped. Some countries even outlawed the exportation of antiviral medication [2]. Recently, several news outlets published stories stating that drug shortages, due to the novel coronavirus (COVID-19), have already begun [3,4,5,6]. China has recently threatened to cut off the supply of life-saving antiviral medication to the United States of America [17].

The world population is an estimated 7.7 billion people with the US population accounting for an estimated 327 million people. The US has stockpiled approximately 28 million courses of the antiviral medication Tamiflu [7] which is used to treat influenza.

Lack of available supply of medication, inability to import new medications or their critical ingredients, and inability to rapidly ramp up medication production to meet the demands of the population will result in increased mortality, prolonged illness and increased viral loads. This directly impacts how contagious someone is, and drastically increases the risk of further spread and the potential of an epidemic or pandemic.

During the Ebola outbreaks, the affected African tribal populations had no access to modern means of transportation. The rapid disease progression coupled with its high mortality made the outbreak amenable to sequestration and quarantining the affected population. These factors resulted in the disease quickly dying off along with the affected population and further spread was prevented.

As recent world events demonstrate, quarantine and sequestration are impractical and ineffective with diseases such as COVID-19 and influenza due to long latency periods; estimated to be as long as two weeks between time of infection and onset of symptoms. The existence of asymptomatic or minimally symptomatic individuals who can spread the disease without even realizing that they have contracted the potentially deadly illness further complicates matters. Another dangerous aspect of the COVID-19 coronavirus outbreak is that it affects large population centers with access to modern means of transportation. All of these factors have contributed to COVID-19 progressing from a small localized outbreak to a world-wide pandemic in less than 90 days. Lack of effective or available treatments and medication shortages can potentially contribute to the spread of infections, thereby turning an epidemic infection into a world-wide pandemic. This jeopardizes the lives of hundreds of thousands if not millions of people as exemplified by the 1918 Spanish Flu Pandemic which killed an estimated 25-50 million people world-wide. The inability to rapidly scale-up medication production, coupled with the limited amount of critical ingredients or woefully inadequate available supply of medications to meet the demands of the population is why on-site recycling of life-saving medication is of paramount importance. The same is true in cases of bioterrorism where a cure must either be made readily available or the limited available supply of medication must be recovered and recycled in order to rapidly expand the potential number of people treated and lives saved.

The idea of recycling medications from human excretion or secretions can understandably be off-putting and seemingly irrelevant to modern society. However, this does not mean it is without value. There are cases in modern medicine where fecal transplants are performed for patients with C. *Difficile* infections or Ulcerative Colitis. At times of crisis such as large-scale pandemics, epidemics, and acts of bioterror, recycling medication may become the only viable option to provide any treatment at all once the supply chain is broken.

During World War II (WW II) Penicillin was difficult to manufacture and in critically short supply. Doctors employed a very time-consuming and complex 21-stage, drug specific, chemical process to recover penicillin from urine during that time of crisis and used it to treat additional patients. The method was published in a medical journal and implemented in military facilities during WW II [16].

This 21-step method was time consuming, very technical, laborious and required a fully functional lab, complete with supplies, reagents and highly trained staff. The time-consuming and complex 21-step chemical method was drug specific to penicillin and would not work to recover any other medications from urine.

Since WW II, we have had world-wide advances in various fields of science and technology. Factory production of medication coupled with their ease of availability have made the thought of recycling medication seemingly irrelevant. However, the above reasoning does not factor in the disruption of the supply chain of medication, or their ingredients, which commonly occur during times of crisis.

We are currently battling a world-wide COVID-19 pandemic, and there is always potential that another world-wide pandemic or large-scale act of bioterrorism will also occur in our lifetime. During these trying times, the needs of the affected population may very well likely exceed the supply of medication, treatment or cure that is available. Thus, there is an urgent need for a practical and immediately implementable modern method for the selective extraction and rapid recycling of medication from body fluid.

BRIEF SUMMARY

The present disclosure relates generally to the selective extraction and rapid recycling of medication from body fluids (at least one body fluid) using a Pressurized Filtration System. In an embodiment, the method to extract and/or recycle at least one medication from at least one body fluid comprises:
(a) Collecting at least one body fluid (non-limiting examples include tears, sweat, saliva, urine, blood, and feces/tissue, which can be liquified, from a subject, preferably but not limited to an animal or mammal, and more preferably a human mammal);
(b) Processing at least one body fluid (e.g., grinding, liquefying, optionally blending, adding chemical/reagents, e.g., anticoagulants);
(c) Depositing said processed body fluid into a filtration system;
(d) Pressurizing the filtration system (>760 mm Hg at 1 Atmosphere Absolute (ATA)) such that the aforementioned processed body fluid is forced through a mesh barrier or filter of the filtration system, wherein bacteria/cells, or other large contaminants in said processed body fluid are blocked from further entering the system beyond the mesh barrier or filter;
(e) Wherein the pressurized filtration system (>760 mm Hg at 1ATA) propels the filtrate from said processed body fluid past the mesh or filter to a nanofilter, forward osmosis filter, or reverse osmosis filter, whereby toxins, and liquid waste remaining in the filtrate are forced through the nanofilter, forward osmosis filter, or reverse osmosis filter (and thereby expelled system) while the medication is trapped in or on the mesh or filter. The trapped medication is simultaneously dried by a constant stream of pressurized air or gas in the system.
(f) Collecting the dried medication from the pressurized filtration system for processing, or storing or potential reuse.

The present disclosure also relates to an innovative system and device for the collection of medications from body fluid via a pressurized filtration system which can be used with minimal equipment, and minimal user training. The system integrates drying as part of the filtration process which is advantageous as it facilitates the easy collection of the medication from the mesh or filter. Furthermore, the system does not rely on a pump, motor, electricity or constant power source.

In an embodiment, the system comprises a closed system which can be pressurized to hyperbaric conditions (>760 mm Hg at 1ATA).

In an embodiment, the system can be pressurized using a compressed air or gas tank, pump, motor, or compressor of any kind including but not limited to human-powered, mechanical, electrical, hydraulic or pneumatic.

In an embodiment, the system utilizes air or compressed gas to propel and force the movement of body fluid across mesh or filters.

In an embodiment, the system comprises a first mesh or filter (or filtration system) configured to prevent the passage (flow-through) of components in animal or mammalian body fluids that have a size greater than about 150, about 200, about 250, about 300, about 350, about 400, about 450, about 500, about 550, about 600, about 650, about 700, about 750, about 800, about 850, about 900, or about 950 Daltons (Da), about 1, about 2, about 3, about 4, about 5, about 10, about 20, about 30, about 40, about 50, about 60, about 70, about 80, about 90, about 100, about 125, about 150, about 175, about 200, about 225, about 250, about 275, about 300, about 325, about 350, about 375, about 400, about 425, about 450, about 475, or about 500 kilodaltons (kDa), while letting smaller components flow through. The system further comprises a second mesh or filter (or filtration system) configured to allow a liquid (e.g., water, or effluent from the first mesh or filter) to flow through while preventing molecules and medications dissolved in the liquid from flowing through.

In an embodiment, the first mesh or filter comprises a microfiltration system, wherein the first mesh or filter is configured to prevent passage of body fluid components selected from the group consisting of cells, bacteria, enzymes, suspended solids, and combinations thereof. In an embodiment, the first mesh or filter has a pore size smaller than 0.02 micron (µm) to exclude the smallest bacteria. Non-limiting examples of an appropriate sized first mesh or filter include Sterlitech 0.01 micron PCT00162x22100 polycarbonate microfilter In an embodiment, the first mesh or filter comprises an ultrafiltration system, wherein the ultrafiltration system is configured to prevent passage of body fluid components selected from the group consisting of suspended solids, bacteria, cells, fats, enzymes, oils, viruses, proteins, macromolecules, and combinations thereof. In an embodiment, the first mesh or filter has a pore size smaller than 0.02 micron (µm) to exclude the smallest bacteria. Non-limiting examples Neo-Pure TL3 ultrafiltration purifier, Wheelton PVDF ultrafiltration water purifier, with 0.01 micron filtration or Geekpure advanced ultrafiltration (UF) water purifier with 0.01 micron filtration.

In an embodiment, the first mesh or filter comprises a nanofiltration system wherein the nanofiltration system is configured to prevent passage of body fluid components selected from the group consisting of viruses, proteins, macromolecules, bacteria, fat, enzymes, suspended solids, and combinations thereof. In an embodiment, the first mesh or filter has a pore size smaller than 0.02 micron (µm) to exclude the smallest bacteria. Non-limiting examples includes AlkaPlus 0.02 micron nanofilter PLU 19761 and Synder NFG 600-800 Da filter.

In an embodiment, the first mesh or filter comprises a microfiltration system and an ultrafiltration system. In an embodiment, the first mesh or filter comprises a microfiltration system and a nanofiltration system. In an embodiment, the first mesh or filter comprises an ultrafiltration system and a nanofiltration system. In an embodiment, the first mesh or filter comprises a microfiltration system, an ultrafiltration system, and a nanofiltration system.

In an embodiment, body fluid is applied to the first mesh/filter or filtration system.

In an embodiment, the first mesh or filter comprises a microfiltration system, and the body fluid applied to the first mesh or filter is first applied to the microfiltration system.

In an embodiment, the first mesh or filter comprises an ultrafiltration system, and the body fluid applied to the first mesh or filter is first applied to the ultrafiltration system.

In an embodiment, the first mesh or filter comprises a nanofiltration system, and the body fluid applied to the first mesh or filter is first applied to the nanofiltration system.

In an embodiment, the first mesh or filter comprises a microfiltration system and an ultrafiltration system, and the body fluid applied to the first mesh or filter is first applied to the microfiltration system and the effluent from the microfiltration system is applied to the ultrafiltration system.

In an embodiment, the first mesh or filter comprises a microfiltration system and a nanofiltration system, and the body fluid applied to the first mesh or filter is first applied to the microfiltration system and the effluent from the microfiltration system is applied to the nanofiltration system.

In an embodiment, the first mesh or filter comprises an ultrafiltration system and a nanofiltration system, and the body fluid applied to the first mesh or filter is first applied to the ultrafiltration system and the effluent from the ultrafiltration system is applied to the nanofiltration system.

In an embodiment, the first mesh or filter comprises a microfiltration system, an ultrafiltration system, and a nanofiltration system, and the body fluid applied to the first mesh or filter is first applied to the microfiltration system, the effluent from the microfiltration system is applied to the ultrafiltration system, and the effluent from the ultrafiltration system is applied to the nanofiltration system.

In an embodiment, the second mesh or filter comprises a reverse osmosis filtration system, wherein the reverse osmosis filtration system is configured to drive a liquid (e.g., water, or effluent from the first filter) through the mesh or filter (membrane) and away from molecules (medications) dissolved in the liquid. Nonlimiting examples of a reverse osmosis Dupont Quick Twist Reverse Osmosis Membrane WFROM1000X 0.001 micron Reverse Osmosis Filter.

In an embodiment, the second filter comprises a mesh or nanofilter wherein the mesh or nanofilter is configured to drive a liquid (e.g., water, or effluent from the first mesh or filter) through the mesh or filter (membrane) and away from molecules (medications) dissolved in the liquid. Nonlimiting examples include: Synder NFW 300-500 Da nanofilter and the Purepro NF270-1812-300 0.0008 micron nanofilter.

In an embodiment, the second mesh or filter comprises a forward osmosis filtration system, wherein the forward osmosis filtration system is configured to drive a liquid (e.g., water, or effluent from the first mesh or filter) through the mesh or filter (membrane) and away from molecules (medications) dissolved in the liquid. Nonlimiting examples of a forward osmosis filter is the Fluid Technology Solutions forward osmosis 0.0007 micron Rainstick water filter.

In an embodiment, effluent from an embodiment of the first mesh/filter is applied to an embodiment of the second mesh/filter or filtration system.

In an embodiment, the body fluid is from a single mammal or collected from multiple mammals. In an embodiment, the mammals are of the same species or different species. In an embodiment, the mammal(s) is/are human(s) (*Homo sapiens*). In an embodiment, the mammals are all taking the same pharmaceutical compound or combination of pharmaceutical compounds, administered to the mammals by any route, including but not limited to oral, rectal, nasal, topical (including buccal and sublingual), transvaginal, and parenteral (including subcutaneous, intramuscular, intravenous, percutaneous, subdural, and intradural).

In an embodiment, the pressurized filtration system uses hyperbaric pressure (>760 mm Hg at 1 ATA) to propel body fluid past a mesh/filters or series of meshes/filters, and the body fluid is filtered through a filtration process comprising multi-stage filtration system connecting a mesh, microfiltration system, ultrafiltration system, reverse osmosis, forward osmosis and/or nanofiltration system to a mesh, microfiltration system, ultrafiltration system, reverse osmosis, forward osmosis and/or nanofiltration system under hyperbaric conditions (>760 mm Hg at 1 ATA) with the purpose of capturing, drying and potentially recycling medications or chemicals from body fluids of subjects treated with or containing at least one pharmaceutical compound in order to potentially treat additional exposed, sick, or infected subjects. This method of recycling medication(s) would also prevent medication from entering the drainage system or otherwise being wasted.

In an embodiment, the medication is contained in body fluid in an unchanged, active, inactive or recoverable form in clinically significant amounts. In an embodiment, the subject from which body fluid is collected from is a human only on the desired medication to be collected. In an embodiment the subject from which body fluid is collected from is on multiple medications, but the non-desired medications are either not contained in that particular body fluid or are not recovered in that body fluid in active form, and/or can be processed out from the desired medication.

In an embodiment, the medication is contained in body fluid in an unchanged, active, inactive or recoverable form in clinically significant amounts. In an embodiment, the subject from which body fluid is collected from is not human, and only on the desired medication to be collected. In an embodiment the subject from which body fluid is collected from is on multiple medications, but the non-desired medications are either not contained in that particular body fluid or are not recovered in that body fluid in active form, and/or can be processed out from the desired medication.

In an embodiment, some of these potentially life-saving medications contained in urine or other body fluids include but are not limited to: Tamiflu [8], Relenza [9], Rapivab [10, 21], Levaquin [11], Chloroquin [12,14], Ciprofloxacin [13], Remdesivir [15], or any other medications or treatments which have been developed or will be developed which are contained in urine in an unchanged, active, inactive or recoverable form in clinically significant amounts. In other words, the instant disclosure is not limited to the foregoing named medications, and a skilled artisan will recognize that any medications that may be present in a bodily fluid in an unchanged active or inactive form may be recovered by practicing the disclosed methods or by using the disclosed system.

In an embodiment, some of these potentially life-saving medications contained in feces or other body fluids include but are not limited to: Ritonavir and lopinavir (16), or any other medications which have been developed or will be developed which are contained in stool in an unchanged, active, inactive or recoverable form in clinically significant amounts. In other words, the instant disclosure is not limited to the foregoing named medications, and a skilled artisan will recognize that any medications that may be present in a bodily fluid in an unchanged active or inactive form may be recovered by practicing the disclosed methods or by using the disclosed system.

Tamiflu, Relenza and Rapivab are antiviral medications with a good track record of successfully treating the flu. They are currently being tested to see if they are effective against the novel coronavirus (COVID-19). Levaquin is an antibiotic used to treat severe hospital acquired pneumonia and several kinds of bioterrorism including inhaled anthrax, and the plague. Chloroquin is an antimalarial drug with some antiviral properties. A recent scientific journal article stated that Chloroquin was found to be effective against the novel coronavirus (COVID-19) in a mutli-center study in China [14, 20]. Ciprofloxacin is an antibiotic used to treat several kinds of bioterrorism including anthrax, the plague, life-threatening meningitis and tularemia. The NIH has announced that antiviral medication Remdesivir has been effective against coronavirus in monkeys and clinical trials in humans have begun [17,18, 20]. The antiretroviral drug Kaletra (Ritonavir/Lopinavir) is very effective against HIV and currently being tested against COVID-19. Whereby, aforementioned medications are non-limiting examples of medications contained in body fluid that can be recovered and potentially recycled by this novel system and device.

In an embodiment, the pressurized filtration system and device are useful for collecting medication from body fluid for potential treatment of diseases and conditions. A further embodiment provides for a method of treating diseases and conditions comprised of applying the medication collected/extracted from the pressurized filtration system discussed in any one of the preceding paragraphs to a subject in need thereof. In a further embodiment, the disease and or condition is caused by a naturally occurring or engineered bacterial or viral infection, bioterrorism pathogen, poison, exposure or toxin.

In an embodiment, the disease can be caused by naturally occurring or engineered bacteria, viruses, poisons, exposures and toxins or a bioterrorism pathogen. Bioterrorism pathogens are bacteria, viruses, poisons, exposures and toxins that are deliberately scattered in the environment causing human or animal disease or death. Bioterror pathogens include, but are not limited to, anthrax (anthrax), plague (pesto), ulcers (pox), tick-borne encephalitis virus (TBEV) (tick-borne encephalitis) and Ebola virus (Ebola). Bioterror pathogens can also include biotoxins, which are toxins produced by certain organisms. Examples of biotoxins include botulinum toxin produced by *Clostridium botulinum* and ricin isolated from castor bean seeds.

In an embodiment, the medication collected from body fluid using the pressurized filtration system discussed above, or pharmaceutically acceptable salts and solvates thereof, is used in the preparation of a medicament or pharmaceutical composition to be potentially applied to a subject in need thereof.

The pharmaceutical compositions prepared from the medication collected from body fluid can be in any form known to those of skill in the art. For instance, in some embodiments the pharmaceutical compositions are in a form of a product for enteral delivery, non-limiting examples include concentrate, dried powder, liquid, capsule, pellet, gel, and pill. In other embodiments, the pharmaceutical compositions of the disclosure are in the form of a product for parenteral administration including but not limited to intranasal, sublingual, auricular, ophthalmic, topical, inhalational, intravenous, intradermal, intramuscular, and subcutaneous administration. The pharmaceutical compositions disclosed herein may also further comprise carriers, binders, diluents, and excipients.

In an embodiment, said medication collected from body fluid can be purified until it has a purity of ≥75%, ≥80%, ≥85%, ≥90%, ≥95%, ≥96%, ≥97%, ≥98%, or ≥99%. In an embodiment, a pharmaceutical composition is provided comprising the medication collected and purified from body fluid, either alone or in combination with at least one additional therapeutic agent, with a pharmaceutically acceptable carrier; and uses of the medication or pharmaceutical composition, either alone or in combination with at least one additional therapeutic agent, in the treatment of diseases and/or condition at any stage of the disease or condition. The methods for treating a clinical indication by the pharmaceutical composition disclosed herein, may be effectuated by administering a therapeutically effective amount of the pharmaceutical composition to a subject in need thereof, this therapeutically effective amount may comprise administration of the prodrug to the subject at 1 mg/kg/day, 2 mg/kg/day, 3 mg/kg/day, 4 mg/kg/day, 5 mg/kg/day, 10 mg/kg/day and 20 mg/kg/day. Alternatively, amounts ranging from about 0.001 mg/kg/day to about 0.01 mg/kg/day, or about 0.01 mg/kg/day to about 0.1 mg/kg/day, or about 0.1 mg/kg/day to about 1 mg/kg/day, or about 1 mg/kg/day to 10 mg/kg/day, about 10 mg/kg/day to about 100 mg/kg/day or in any clinically effective dose are also contemplated.

A further object of the disclosure is a kit, comprising the pressurized filtration system and device disclosed herein for treatment, prevention, and or elimination of conditions or diseases, such as bacterial or viral infections, toxins, poisons, exposures and related conditions or morbidities. The composition of the kit may comprise a further purification device to purify the medication, and at least one carrier, at least one binder, at least one diluent, at least one excipient, at least one other therapeutic agent, or mixtures thereof. A further object of the disclosure is a kit comprising the purified medication discussed herein and at least one carrier, at least one binder, at least one diluent, at least one excipient, at least one other therapeutic agent, or mixtures thereof.

One aspect of the present disclosure is the medication collected and purified from body fluid disclosed herein as well as the intermediates as used for their synthesis.

While certain features of this invention shown and described below are pointed out in the annexed claims, the invention is not intended to be limited to the details specified, since a person of ordinary skill in the relevant art will understand that various omissions, modifications, substitutions, and changes in the forms and details of the invention illustrated and in its operation may be made without departing in any way from the spirit of the present invention. No feature of the invention is critical or essential unless it is expressly stated as being "critical" or "essential."

These and other features, aspects, and advantages of embodiments of the present disclosure will become better understood with regard to the following descriptions, claims, and accompanying drawings explained below.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

FIG. 1 is a schematic diagram of an embodiment of the pressurized filtration system of the instant disclosure.

FIG. 2 is a schematic diagram of an embodiment of the pressurized filtration system of the instant disclosure.

FIG. 3 shows an embodiment of a pressurized filtration system and device discussed herein to collect medication from body fluid.

FIG. 4 shows an embodiment of a pressurized filtration system and device discussed herein to collect medication from body fluid.

FIG. 5 shows readily available filtration system components based on size of the components to be recovered from body fluid.

DETAILED DESCRIPTION

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

In an embodiment, a method is provided to recover medications from body fluids. In an embodiment, the method is accomplished through the use of a pressurized filtration device with the specific purpose of capturing and potentially recycling medications from body fluid (see, e.g., FIG. 1).

The disclosed pressurized filtration system and method rely on the scientific certainty that red blood cells and bacteria are very large, and the main components and toxins in body fluid are very small. In the chart below I have included the main toxins from urine as an example to demonstrate this. As evidenced by their molecular weights/diameters (ammonia, NaCl, Urea, Creatinine, CaOx, Uric Acid and H2O) are approximately ⅓ the size of the medications. Urobilin gives urine it's color, is in a very low amount in urine and not particularly toxic. By comparison, medications (such as Tamiflu, Chloroquin, Relenza, Levaquin, Rapivab and Ciprofloxacin) are significantly larger than the size of the toxins contained in urine, but are orders of magnitude smaller than bacteria, red blood cells, and white blood cells (TABLE 1).

TABLE 1

Sizes and densities of average toxins in urine, compared to medications

| Chemical | Mol Wt (g/mol) | Density (g/cm³) | Spherical Dia (nm) | |
|---|---|---|---|---|
| Ammonia | 17.031 | 0.88 | 0.394 | |
| Salt (NaCl) | 58.44 | 2.16 | 0.441 | |
| Urea | 60.06 | 1.32 | 0.525 | |
| Creatinine | 113.12 | 1.09 | 0.69 | |
| Calcium Oxalate | 128.097 | 2.12 | 0.577 | |
| Uric Acid | 168.1103 | 1.87 | 0.658 | |
| Urobilin (low amt) | 590.71 | 1.32 | 1.12 | |
| Water (H₂O) | 18.015 | 1 | 0.385 | |
| | | | | % Excreted Unchanged or Active Metabolite in Urine |
| Tamiflu | 410.4 | 1.08 | 1.064 | 90 |
| Chloroquine | 319.872 | 1.1 | 0.973 | 70 |
| Relenza | 332.31 | 1.75 | 0.844 | 90 |
| Levaquin | 361.368 | 1.5 | 0.914 | 85 |
| Rapivab | 328.407 | 1.4 | 0.906 | 90 |
| Ciprofloxacin HCl | 385.82 | 1.46 | 0.943 | 45 |
| Remdesevir | 602.576 | 1.5 | 1.084 | Information not available |

In an embodiment, the pressurized Filtration system comprises pressurized air or gas (30) used to propel at least one body fluid through the pressurized filtration system. Non-limiting examples of sources for pressurized gas include: a compressed air or gas tank, pump, motor, compressor of any kind including but not limited to human-powered, mechanical, electrical, hydraulic, or pneumatic.

Figure 3:
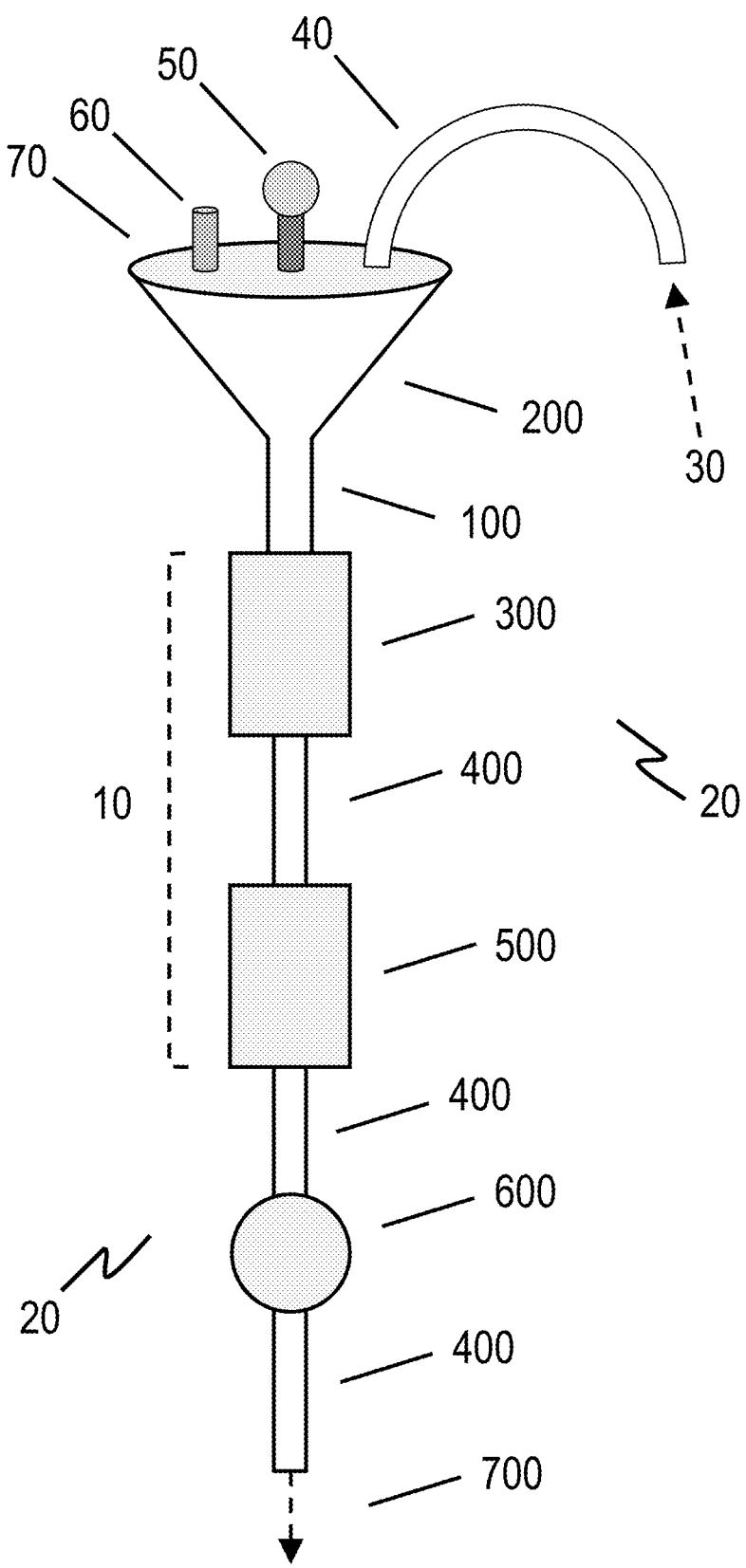
Figure 4:
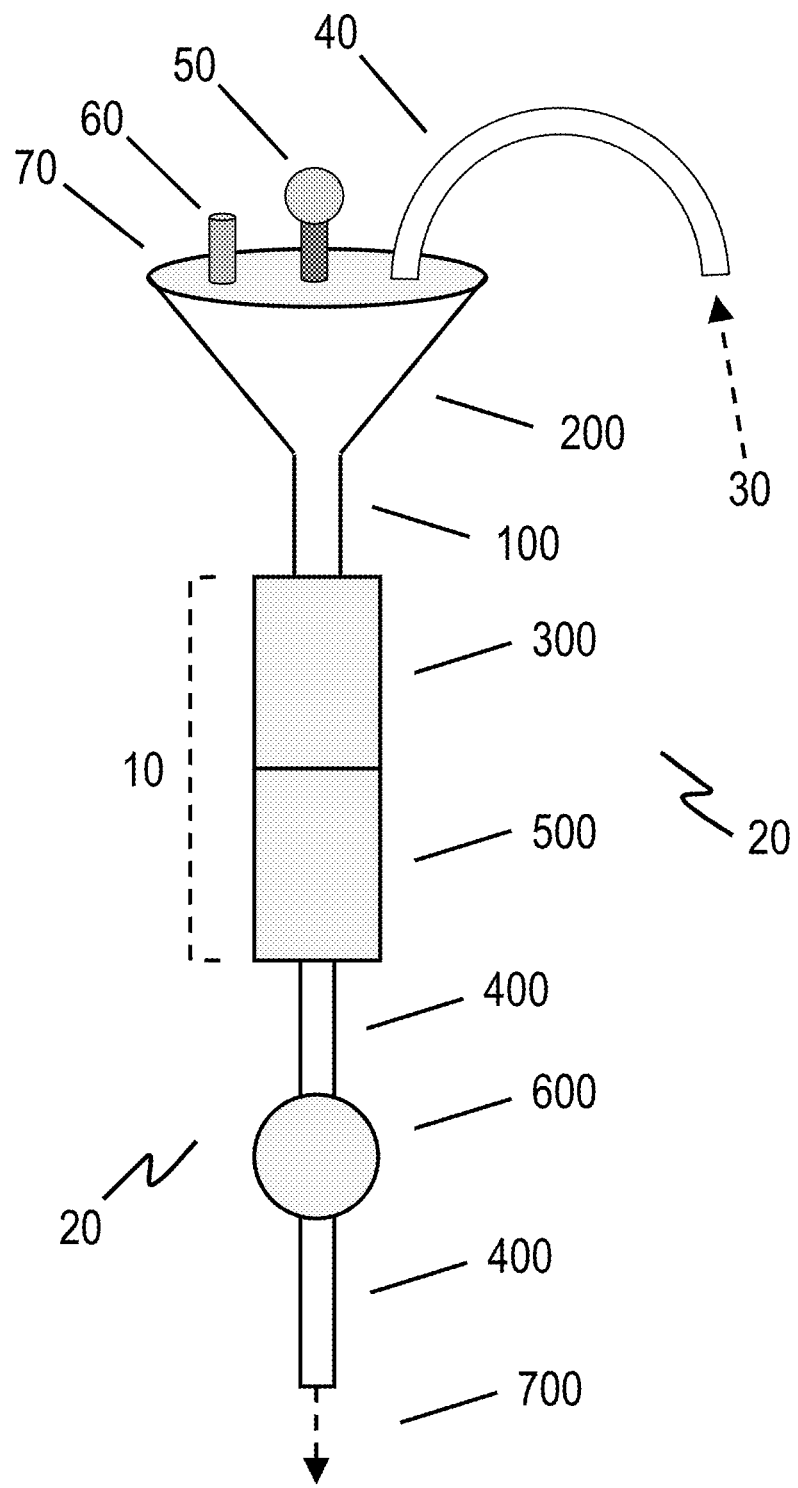
Figure 5:
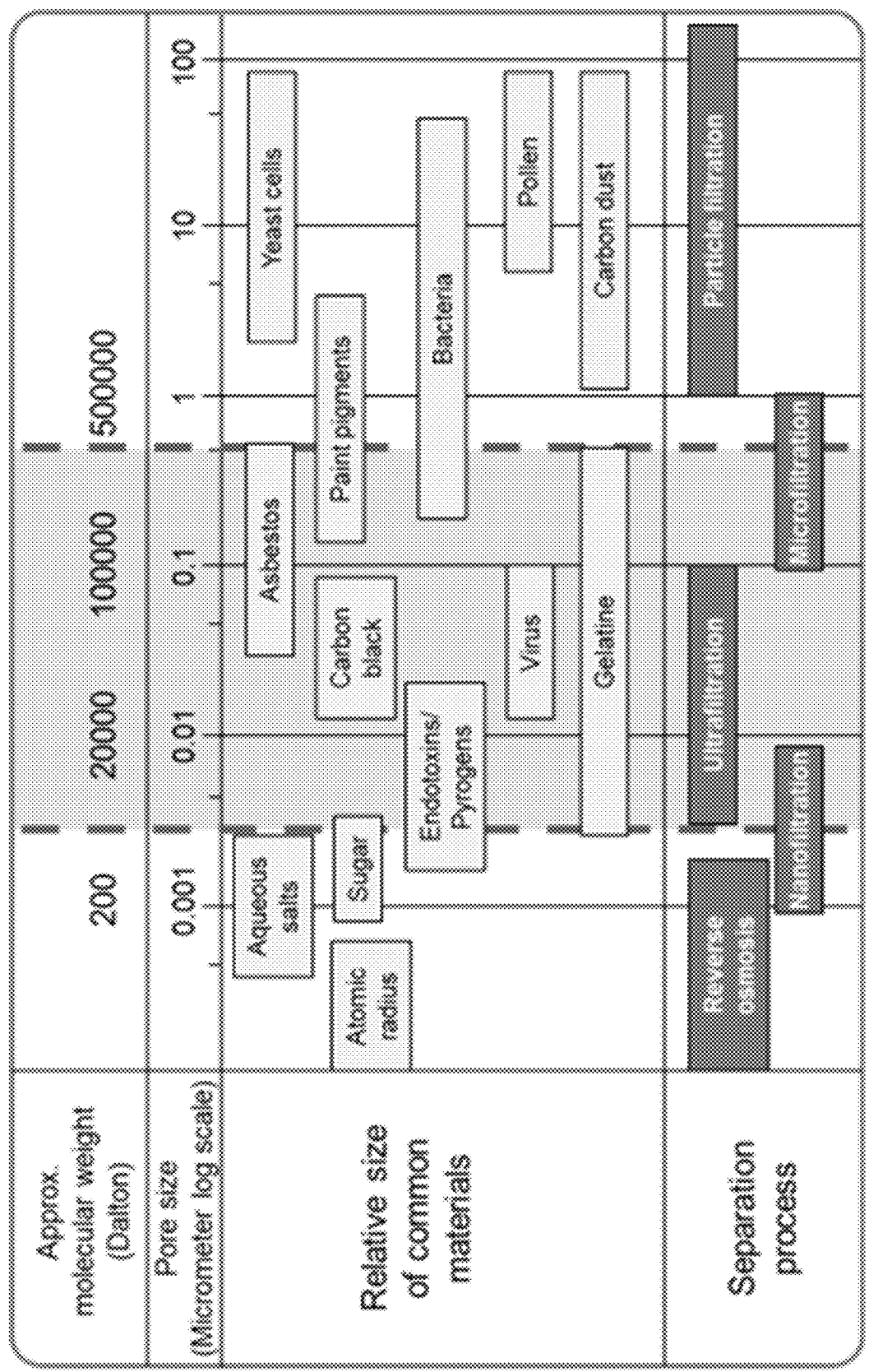

In an embodiment, the pressurized filtration system comprises a nozzle, hole, or access point of any kind in which to connect to a hose (40) or directly or indirectly to a device enabling the system to be pressurized (see FIGS. 3 & 4, where tube (40) connects to lid (70) of a receptacle (200)). While FIGS. 3 and 4 illustrate a hose (40) between a source of pressure (30) and the device (20), in an embodiment the hose may be absent and the device (20) may be connected directly to a pressure source (30). In this embodiment, a valve (not shown) may be interposed between and in line with the device (20) and the pressure source (30).

In an embodiment, the pressurized filtration system comprises at least one pressure relief valve (60) to prevent over-pressurization, however because pressure can be otherwise regulated (e.g., low pressure pump or flow regulator), it is not essential. The attachment point of the pressure relief valve (60) as shown by FIGS. 3 and 4 is illustrative and not intended to be limiting. The pressure relief valve (60), if used, may be attached at any point on the device (20). In a further embodiment, more than one pressure relief valve (60) is contemplated (at least one pressure relief valve (60)), which may be attached at any point on the device (20).

The attachment point of the pressure source (30) to the device (20) as shown by FIGS. 3 and 4 is illustrative and not intended to be limiting. The pressure source (30) connection to the device (20) may occur at any point of the device (20) such that the pressure is applied in a manner that forces the at least one bodily fluid toward the first mesh or filter (300) and the eluate from the first mesh or filter (300) toward the second mesh or filter (500).

In an embodiment the pressurized filtration system comprises at least one pressure gauge (50) to enable monitoring of the system, however because pressure can be otherwise regulated to prevent over-pressurization (e.g., low pressure pump or flow regulator), pressure monitoring is not essential. The attachment point of the pressure gauge (50) as shown by FIGS. 3 and 4 is illustrative and not intended to be limiting. The pressure gauge (50), if used, may be attached at any point on the device (20). In a further embodiment, more than one pressure gauge (50) is contemplated (at least one pressure gauge (50)), which may be attached at any point on the device (20).

In an embodiment the pressurized filtration system comprises at least one flow regulator (not shown) for added safety, however it is not an essential component to the design because regulating the flow can be accomplished in other ways (e.g. low-pressure pump).

Figure 2:
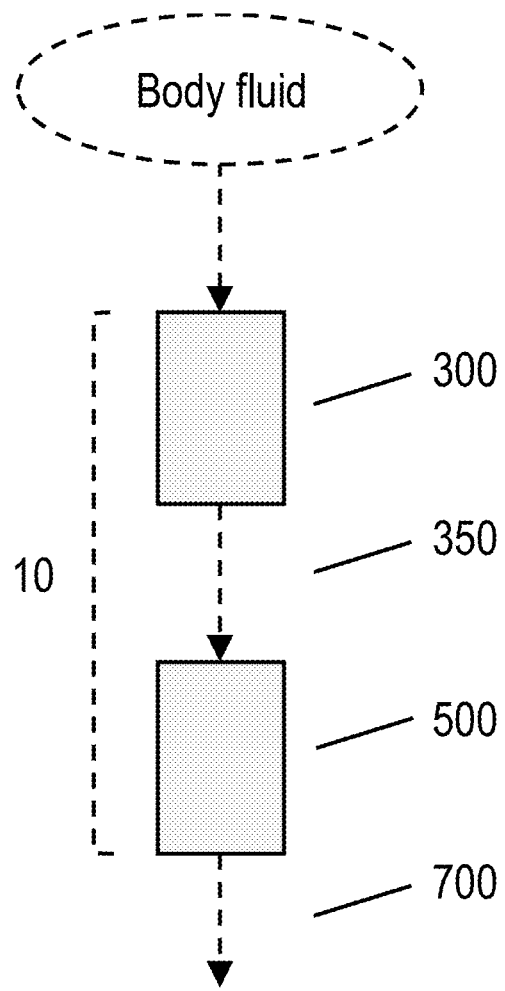

In an embodiment the pressurized filtration system (10) comprises a source of pressure (30), a first mesh or filter (300) to block bacteria and cells, and a second mesh or filter (500) configured to allow all of the toxins and liquid (700) to pass through the second mesh or filter (500) while leaving dissolved molecules (i.e., the desired medication) behind in or on the second mesh or filter (see FIGS. 1 & 2).

In an embodiment, the first mesh or filter (300) and the second mesh or filter (500) are in fluid connection to one another as a single unit (see FIG. 1). In an embodiment, the first mesh or filter (300) and the second mesh or filter (500) are in fluid connection to one another via a connector (400). In an embodiment, the connector (400) is tubing (see FIG. 3).

In an embodiment, the pressurized filtration system (10) further comprises a tube (100) with a receptacle or access point (200) to add body fluid into the first mesh or filter (300), as shown in FIGS. 3 & 4. The receptacle (200) can be closed by a lid (70) after at least one body fluid is added to the receptacle (200). The lid (70) or receptacle (200) is connected to a source of gas pressure (30) such as pressurized air, via a tube or hose (40) or directly or indirectly to a source of pressure, whereby once the lid (70) is closed (secured) to the receptacle (200) and the gas pressure source

(30) applied, the pressurized gas flows through the tube or hose (40) into the system (10) via the connection between tube or hose (40) or other method of directly or indirectly connecting pressure from a pressure source and the lid (70) or receptacle (200). The lid (70) or receptacle (200) optionally contains a pressure gauge (50) and further optionally contains a pressure regulator/pressure relief valve (60). The pressure regulator can optionally be placed at the pressure source, connection between the pressure source and device, or at other locations on the device itself. The pressure relief valve can optionally be placed at the pressure source, connection between the pressure source and device, or at other locations on the device itself. The pressure gauge can optionally be placed at the pressure source, connection between the pressure source and device, or at other locations on the device itself.

In an embodiment, the Pressurized filtration system (10) is a device (20) which comprises a source of pressure (30), a first mesh or filter (300) to block bacteria and cells, and a second mesh or filter (500) configured to allow all of the toxins and liquid (700) to pass through while leaving dissolved molecules (i.e. the desired medication(s)) behind (see FIGS. 3 & 4). The first mesh or filter (300) and the second mesh or filter (500) may be in fluid connection to one another as a single unit (FIG. 4) or may be in fluid connection to one another via a connector (400), as in FIG. 3, which may be tubing.

The device (20) may further comprise a valve (600), such as a stopcock or a one-way valve, in fluid connection to the second mesh or filter (500) via a connector (400), and the valve (600) may further comprise a connector or tubing (400) for effluent (700), as in FIGS. 3 & 4. Micro-, ultra- and nano-reverse osmosis-, and forward osmosis filtration (first) and reverse osmosis, forward osmosis and/or nano-filtration (second) filters are known, but a pressurized filtration system has not yet to be used to recover and recycle medication from body fluid.

There are numerous advantages and benefits to using the pressurized filtration system discussed herein, as opposed to the previously discussed 21-stage drug-specific complex chemical process which was utilized during WW II to remove and recycle Penicillin from urine, including:
  Cost effectiveness: meshes and filters are cheap and can be cleaned/reused. They don't need to be sterile because medication can be processed after recovery to be sterilized if needed.
  Expediency: this is a much faster process than had previously been considered.
  Rapid deployment: this system/method could be deployed across the world in hours
  Comparatively easy to use and requires minimal training.
  Self-contained unit, complex lab equipment is not needed to perform the extraction
  Does not rely on mixing dangerous acids/bases to perform extraction, which puts people at risk for injury
  Can be used to selectively recover various existing and future developed medications rather than specific only to Penicillin This Pressurized Filtration System is a dramatic innovation over a previously described theoretical rudimentary process described in a 1991 German patent (DE4129041). Their method was never put into practice, most likely due to the fact that as described, it was not a fully functioning process due to practical obstacles to implementation. This realization would have been obvious to those skilled in the art. Said theoretical process also required a "pump" to push body fluid through either: different size filters or alternatively utilized a "chromatographic filtering process". In theory the sludge-like compound which would have completely permeated the poorly described filter, was theoretically removed from the membrane, and in a separate step the medication subsequently required vacuum drying and further processing. In practice, someone skilled in the art would understand that within itself, the extraction of medication from a sludge-impregnated filter is a complex and multi-step process.

Advantages of this novel method utilizing a pressurized filtration system over the previously described theoretical, and impractical German method include:
  Hyperbaric pressure (>760 mm Hg at 1 ATA) used to propel fluid through membranes rather than a pump. Less moving parts equates to less risk of mechanical failure or pump failure. In an aspect, the filtration system discussed herein does not include a pump.
  No electricity is required with a pressurized filtration system which enables rapid field deployment and use in areas where electricity is not available. In an aspect, the filtration system discussed herein does not use electricity.
  A pressure driven system rather than pump driven system allows for use under harsh or extreme conditions such as extreme heat or dust which could cause mechanical failure in the German design due to overheating or clogging the pump.
  Hyperbaric pressurize (>760 mm Hg at 1 ATA) can be obtained using a compressed air or gas tank, or pump, motor, compressor of any kind including but not limited to human-powered, mechanical, electrical, hydraulic, or pneumatic.
  Propelling the system with pressurized air or gas (>760 mm Hg at 1 ATA) results in more efficiency and less steps in the process. Filtration and drying are simultaneously performed due to constant movement of compressed air or gas over the mesh or filter once body fluid has passed. The heating effect of compressing gas flowing through a system also assists in the drying process.
  Due to simultaneous drying, heating and recovery of medications, a dry product remains on the mesh or filter which is easier and more practical to remove than previously described sludge-impregnated filter which would then require a complex multi-step process for extracting the medication from the filter prior to even attempting to dry it.
  Antimicrobial effect of streaming hyperbaric gas or air over a mesh, filter or surface contributes to a self-cleaning effect.
  Little training/education needed to run the system as opposed to a system using complex scientific machinery such as a chromatographic filtering process.
  Inexpensive to make and does not require expensive lab equipment or pumps.

While some meshes or filters do exist that have chemical properties/charges, the typical mesh or filter removes materials based only on size. The pressurized filtering system used depends on the types of mesh or filters available. In an embodiment, the subject from which body fluid is collected to recover medication is a young healthy subject, who is only on the medication to be recovered. However, as many drugs are not contained in body fluid in an active form and drug processing is possible, subjects on multiple medications can also be candidates for this process. In an embodiment, the subject from which the body fluid is collected to recover medication is a subject on multiple medications, wherein the non-desired medications are either not contained in that particular body fluid and/or can be processed out from the desired medication to be recovered.

The present disclosure also provides methods of collecting medication from body fluid (see FIGS. 1 & 2), comprising:

Collecting body fluid containing a medication from suitable patients;

Depositing the body fluid inside of the receptacle (200) of the pressurized filtration system and pressurizing the system.

The pressurized system forces the collected and prepared body fluid through a first mesh or filter (300);

Propelling the effluent from the first mesh or filter (300) through a second mesh or filter (500) while under pressure (30), wherein the medication is retained in or on the second mesh or filter (500) while the liquid passes through the second mesh or filter (500) as effluent (700). The medication retained in or on the second mesh or filter (500) is dried by the pressurized stream of air or gas.

The present disclosure also provides for a method to collect medication from body fluid (FIGS. 3 & 4) comprising:

Collecting body fluid containing a medication from suitable patients;

depositing the collected body fluid into a device (10) disclosed herein (see, e.g., FIG. 1), Forcing the collected body fluid through a first mesh or filter (300), under hyperbaric conditions (>760 mm Hg at 1ATA) thereby removing bacteria/cells and large contaminants;

Propelling the effluent from the first mesh filter (300) under pressure (30) through a second mesh or filter (500), wherein the medication is retained in or on the second mesh or filter (500) while the liquid passes through the second mesh or filter (500) as effluent (700). The medication retained in or on the second mesh or filter (500) is simultaneously dried by the constant pressurized stream of air or gas.

The dried medication is then collected from the second mesh or filter (500) and processed (tested for purity/concentration, and sterilized if needed) and potentially recycled to treat additional exposed, sick or infected subjects.

A further embodiment provides for a method of treating diseases and conditions comprising applying the (purified) medicine collected/extracted from a pressurized filtration system discussed in any one of the preceding paragraphs to a subject in need thereof.

In an embodiment, the medications to be extracted from body fluid comprises any medication which is contained in clinically significant amounts in an unchanged, active, inactive and recoverable form in that particular body fluid, and are amenable to capturing and recycling using my invention. In a further embodiment, the medications include but are not limited to: Tamiflu [8], Relenza [9], Rapivab [10,21], Levaquin [11], Chloroquin [12,14], Ciprofloxacin [13], Remdesivir [15], Ritonivir/Lopinivir [16].

In a further embodiment, the term medications includes medications that currently exist or will be developed or discovered for the treatment of exposed, sick, or infected subjects.

In a further embodiment, the term medication includes naturally occurring or engineered hormones, chemicals, antibodies, lipids, enzymes, proteins or products which currently exist or will be developed for the treatment of deficient, exposed, sick, or infected subjects that can be collected from body fluid in an unchanged, active, inactive and recoverable form.

In an embodiment, the medications collected from body fluid according to the disclosure are isolated and purified in a manner known per se, e.g., by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present disclosure which possess a sufficiently basic or acidic functionality, may result in the formation of a salt, such as, in the case of a compound of the present disclosure which is sufficiently basic, a trifluoroacetate or formate salt for example, or, in the case of a compound of the present disclosure which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present disclosure may not fully remove traces of co-solvents, especially such as formic acid or trifluoroacetic acid, to give solvates or inclusion complexes. The person skilled in the art will recognize which solvates or inclusion complexes are acceptable to be used in subsequent biological assays. It is to be understood that the specific form (e.g., salt, free base, solvate, inclusion complex) of a compound of the present disclosure as isolated as described herein is not necessarily the only form in which said compound can be applied to a biological assay in order to quantify the specific biological activity.

One aspect of the disclosure is salts of the collected medication according to the disclosure including all inorganic and organic salts, especially all pharmaceutically acceptable inorganic and organic salts, particularly all pharmaceutically acceptable inorganic and organic salts customarily used in pharmacy.

It is a further object of the disclosure to provide collected medications disclosed herein, methods of purifying the medications well established in the art, and methods of using the purified medications for treating of a disease in a subject in a subject thereof.

As used herein, "treating" means administering to a subject a pharmaceutical composition to ameliorate, reduce, lessen or eliminate the symptoms of a disease, condition, deficiency, disorder or the disease itself. As used herein, "treating" or "treat" describes the management and care of a subject for the purpose of combating or eliminating a disease, condition, deficiency or disorder and includes the administration of a compound disclosed herein, or a pharmaceutically acceptable salt, polymorph or solvate thereof, to alleviate the symptoms or complications of a disease, condition or disorder, or to eliminate the disease, condition or disorder. The term "treat" may also include treatment of a cell in vitro or an animal model. As used herein, "subject" or "subjects" refers to any animal, not limiting examples include mammals such as rodents (e.g., mice or rats), dogs, primates, lemurs or humans.

Treating diseases may result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating diseases may result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating diseases may result in a decrease in the mortality rate of a population of treated subjects in comparison to a population receiving carrier alone. Treating cancer may result in a decrease in the mortality rate of a population of treated subjects in comparison to an untreated population. Treating diseases may result in a decrease in the mortality rate of a population of treated subjects in comparison to a population receiving no therapy, or monotherapy with a drug that is not a compound disclosed herein, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

REFERENCES

1. Taubenberger J K, Morens D M (January 2006). "1918 Influenza: the mother of all pandemics". Emerging Infectious Diseases. 12 (1): 15-22. doi:10.3201/eid1201.050979. PMC 3291398. PMID 16494711.
2. available at: reuters.com/article/flu-greece/greece-bans-anti-flu-drug-exports-idUSL138081120090501
3. available at: nytimes.com/2020/02/28/health/drug-coronavirus-shortage.html
4. available at: thehill.com/changing-America/well-being/prevention-cures/485216-first-coronavirus-related-drug-shortage-hits-us
5. available at: cnbc.com/2020/02/28/fda-reports-first-coronavirus-related-drug-shortage.html
6. available at: snopes.com/ap/2020/02/28/us-reports-first-drug-shortage-tied-to-coronavirus-outbreak/7. available at: uschamber.com/how-much-tamiflu-us-government-stockpiling
8. available at: fda.gov/media/77829/download
9. available at: ncbi.nlm.nih.gov/pubmed/10429835
10. available at: ncbi.nlm.nih.gov/books/NBK547844/
11. available at: accessdata.fda.gov/drugsatfda_docs/label/2006/020634s040,020635s043,021721s00 7lbl.pdf
12. available at: glowm.com/resources/glowm/cd/pages/drugs/c048.html
13. available at: fda.gov/media/75526/download
14. available at: ncbi.nlm.nih.gov/pubmed/32074550
15. A Method for the recovery of penicillin from the urine, Lawrence Sophian M D. J. Lab and Clin Med, St. Louis, 29:769-771, July 1944. US Marine Hospital, Staten Island, N.Y. (available at: archive.org/stream/in.ernet.dli.2015.116336/2015.116336. The-Journal-Of-Laboratory-And-Clinical-Medicine29_djvu .txt)
16. available at: www.accessdata.fda.gov/drugsatfda_docs/labeV2007/021226s022lbl.pdf available at www-.foxnews.com/world/chinese-deny-americans-coronavirus-drugs

What is claimed is:

1. A method for extracting and/or recycling at least one medication from a body fluid comprising:
    (a) Collecting a body fluid from a subject,
    (b) Processing the body fluid,
    (c) Passing the body fluid through a pressurized filtration system, wherein the bacteria/cells, contaminants, toxins, and liquid waste are removed and the at least one medication is simultaneously trapped and dried in the pressurized filtration system, and
    (d) Collecting the at least one medication from the pressurized filtration system;
wherein the pressurized filtration system comprises a first mesh or filter and a second mesh or filter, and step (c) comprises:
    passing the collected body fluid through the first mesh or filter, and
    directing the effluent from the first mesh or filter through the second mesh or filter, wherein at least one medication is retained by the second mesh or filter while the liquid or liquid waste passes through the second mesh or filter as effluent.

2. The method according to claim 1, wherein the first mesh or filter and the second mesh or filter are in fluid connection to one another as a single unit or via a connector.

3. The method according to claim 1, wherein the first mesh or filter is configured to prevent the passage of components in body fluid that have a size greater than about 1,000 Da while permitting passage of smaller components, and the second mesh or filter is configured to allow passage of effluent from the first mesh or filter while preventing passage of the at least one medication dissolved in the effluent.

4. The method according to claim 1, wherein
    the first mesh or filter comprises at least one mesh or filter selected from the group consisting of a microfiltration system, an ultrafiltration system, mesh, reverse osmosis, forward osmosis, and a nanofiltration system, and wherein the first mesh or filter is configured to prevent passage of body fluid components selected from the group consisting of suspended solids, bacteria, cells, fats, enzymes, oils, viruses, proteins, macromolecules, and combinations thereof, and the second mesh or filter comprises a mesh, reverse osmosis filtration system, forward osmosis system or a nanofiltration system, wherein the mesh, reverse osmosis filtration, forward osmosis filtration system and/or nanofiltration system is configured to drive the body fluid through the mesh or filter while under hyperbaric pressure and away from molecules dissolved in the liquid.

5. The method according to claim 1, wherein the at least one medication to be extracted and/or recycled from body fluid comprises any medication which is eliminated in clinically significant amounts in an unchanged, active, inactive, metabolite and recoverable form in the body fluid.

6. The method according to claim 1, wherein the at least one medication to be extracted and/or recycled from body fluid is oseltamivir.

7. The method according to claim 1, further comprising testing the medication collected from the pressurized filtration system for purity or concentration, optionally sterilizing the medication, and recycling or storing the medication.

8. The method according to claim 1, wherein b) comprises blending and/or mixing the fluid with anticoagulants or other reagents/chemicals to process the body fluid.

9. The method according to claim 1, wherein the system is pressurized to >760 mm Hg at 1 Atmosphere Absolute.

10. The method according to claim 1, wherein the collected medication is dried by a stream of pressurized air or gas in the pressurized filtration system.

11. The method according to claim 1, wherein the first mesh or filter is configured to prevent the passage of components in body fluid that have a size greater than about 300 Da, and the second mesh or filter is configured to allow passage of effluent from the first mesh or filter while preventing passage of at least one medication dissolved in the effluent.

12. The method according to claim 1, wherein the first mesh or filter is configured to prevent the passage (flow-through) of components in body fluid that have a size greater than about 100 KDa, and the second mesh or filter is configured to allow passage of effluent from the first mesh or filter while preventing passage of at least one medication dissolved in the effluent.

13. The method according to claim 1, wherein the at least one medication to be extracted and/or recycled from body fluid is zanamivir.

14. The method according to claim 1, wherein the at least one medication to be extracted and/or recycled from body fluid is peramivir.

15. The method according to claim 1, wherein the at least one medication to be extracted and/or recycled from body fluid is levofloxacin.

16. The method according to claim 1, wherein the at least one medication to be extracted and/or recycled from body fluid is chloroquine.

17. The method according to claim 1, wherein the at least one medication to be extracted and/or recycled from body fluid is ciprofloxacin.

18. The method according to claim 1, wherein the at least one medication to be extracted and/or recycled from body fluid is lopinavir and/or ritonavir.

19. The method according to claim 1, wherein the at least one medication to be extracted and/or recycled from body fluid is remdesivir.

* * * * *